(12) United States Patent
Nguyen

(10) Patent No.: US 7,313,501 B2
(45) Date of Patent: Dec. 25, 2007

(54) METHOD AND SYSTEM FOR DETERMINING THE LOCATION OF A POTENTIAL DEFECT IN A DEVICE BASED ON A TEMPERATURE PROFILE

(75) Inventor: Dat T. Nguyen, Murphy, TX (US)

(73) Assignee: Texas Instruments Incorporated, Dallas, TX (US)

( * ) Notice: Subject to any disclaimer, the term of this patent is extended or adjusted under 35 U.S.C. 154(b) by 49 days.

(21) Appl. No.: 11/048,996

(22) Filed: Feb. 2, 2005

(65) Prior Publication Data

US 2006/0173647 A1    Aug. 3, 2006

(51) Int. Cl.
*G01K 17/00* (2006.01)
(52) U.S. Cl. ............ 702/136; 702/155; 702/172; 374/126; 374/128; 219/121.8; 219/121.78
(58) Field of Classification Search ......... 702/136, 702/155, 31, 172; 700/17, 83; 374/126, 374/128; 219/121.8, 121.78
See application file for complete search history.

(56) References Cited

U.S. PATENT DOCUMENTS

| | | | | |
|---|---|---|---|---|
| 5,907,820 A | * | 5/1999 | Pan | 702/155 |
| 6,095,679 A | * | 8/2000 | Hammiche et al. | 374/43 |
| 6,123,766 A | * | 9/2000 | Williams et al. | 117/85 |
| 6,566,885 B1 | * | 5/2003 | Pinto et al. | 324/501 |
| 6,747,245 B2 | * | 6/2004 | Talwar et al. | 219/121.8 |

* cited by examiner

*Primary Examiner*—Michael P. Nghiem
*Assistant Examiner*—Hien Vo
(74) *Attorney, Agent, or Firm*—Yingsheng Tung; Wade James Brady, III; Frederick J. Telecky, Jr.

(57) ABSTRACT

According to one embodiment of the invention a method for determining the location of a potential defect in a device includes scanning a surface of the device with a temperature sensor while operating the device. The method also includes measuring a temperature of the device by a temperature sensor at a plurality of locations while scanning. Based upon the measured temperatures, a temperature profile is constructed for the device. The method also includes comparing the constructed temperature profile to a reference profile to determine a location of the potential defect in the device.

19 Claims, 2 Drawing Sheets

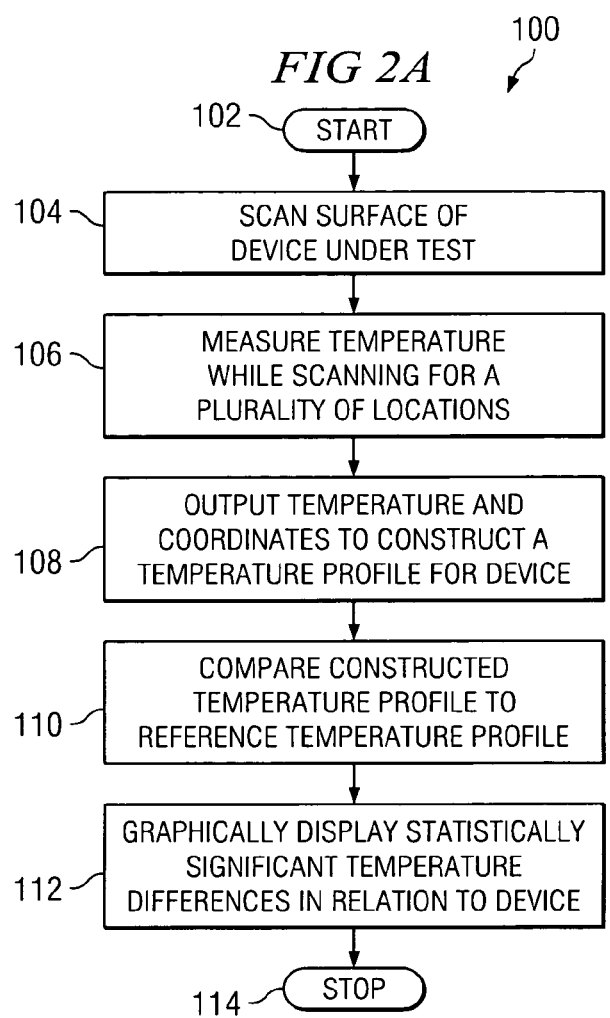
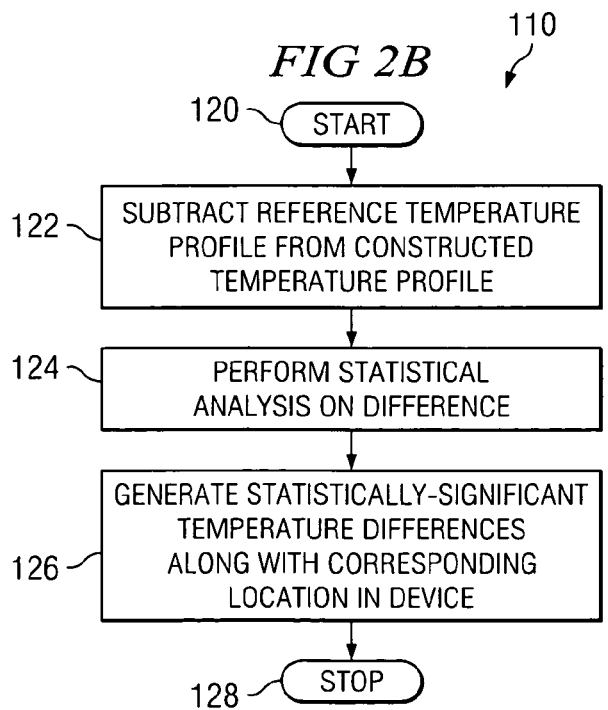

METHOD AND SYSTEM FOR DETERMINING THE LOCATION OF A POTENTIAL DEFECT IN A DEVICE BASED ON A TEMPERATURE PROFILE

TECHNICAL FIELD OF THE INVENTION

This invention relates generally to device testing and more particularly a method and system for determining the location of a potential defect in a device based upon a temperature profile of the device.

BACKGROUND

Semiconductor devices are prevalent in today's society. An important consideration in the manufacture of a semiconductor device is the ability to efficiently locate areas in the semiconductor device that are operating improperly. Doing so may be difficult because typical semiconductor devices involve enormous amounts of circuitry, and it can often be difficult to identify particular portions of the semiconductor device that are operating improperly, resulting in improper operation of the overall device. The ability to locate a specific location of a defect in a device is important in areas other than semiconductor devices, such as in the nanotechnology field, as well as many others.

SUMMARY

According to one embodiment of the invention a method for determining the location of a potential defect in a device includes scanning a surface of the device with a temperature sensor while operating the device. The method also includes measuring a temperature of the device by a temperature sensor at a plurality of locations while scanning. Based upon the measured temperatures, a temperature profile is constructed for the device. The method also includes comparing the constructed temperature profile to a reference profile to determine a location of the potential defect in the device.

Some embodiments of the invention provide numerous technical advantages. Some, none, or all embodiments may benefit from the below-described advantages. According to one embodiment, a potential location of a defect in a device may be identified through comparison of a generated temperature profile to a reference temperature profile. In some embodiments, a very fine resolution for the temperature profile may be obtained. This provides the ability to quickly locate a potential location of a defect in a device, which otherwise may be a time-consuming process.

Other technical advantages will be readily apparent to one skilled in the art.

BRIEF DESCRIPTION OF THE DRAWINGS

For a more complete understanding of the present invention and its advantages, references now made to the following description, taken in conjunction with the accompanying drawings, in which:

FIG. 2A is a flowchart illustrating a method for determining a location of a defect in a semiconductor device based on a temperature profile of the semiconductor device; and FIG. 2B is a flowchart illustrating a method for comparing a measured temperature profile of a semiconductor device to a reference temperature profile of the semiconductor device according to the teachings of the invention.

DETAILED DESCRIPTION

Embodiments of the present invention and its advantages are best understood by referring to FIGS. 1A through 2B of the drawings, like numerals being used for like and corresponding parts of the various drawings.

Figure 1A:
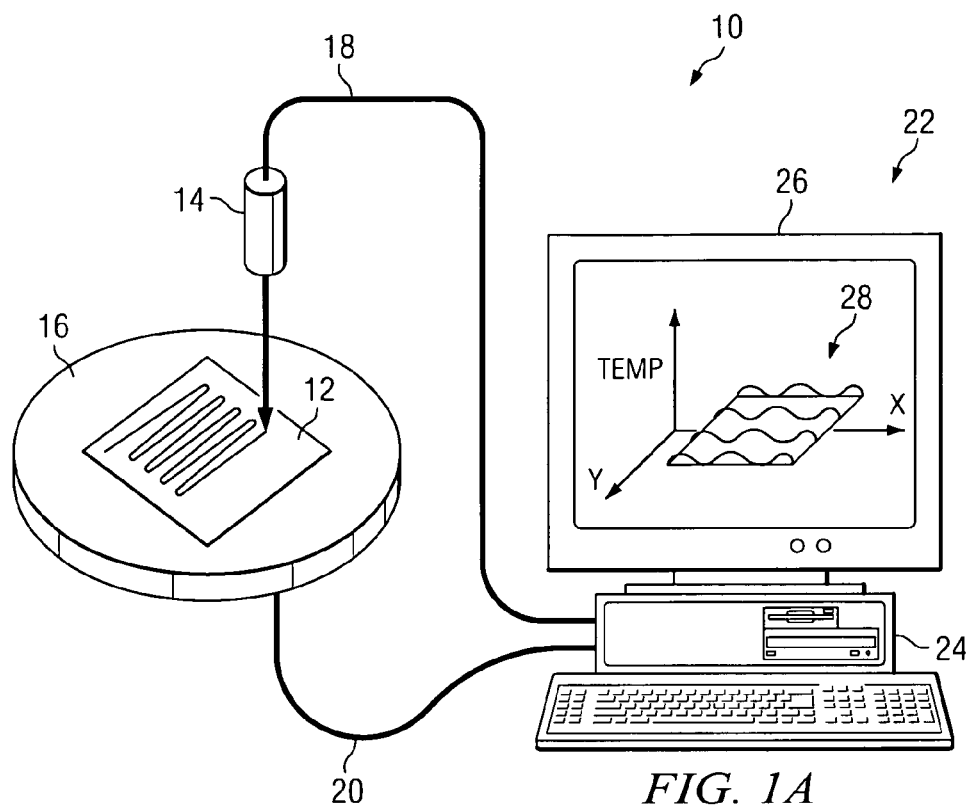
FIG. 1A is a schematic diagram illustrating a system for determining a location of a potential defect in a semiconductor device based on a measured temperature profile of the semiconductor device.

FIG. 1A is a schematic diagram illustrating a system 10 for determining a location of a defect in a semiconductor device based on a temperature profile of the semiconductor device according to the teachings of the invention. Although the invention is described in the context of determining a defect in a semiconductor device, the teachings of the invention are also applicable to devices other than semiconductor devices, such as devices used in semiconductor design debugs (in term of integrated circuitry heat propagation, current flow analysis, and current consumption analysis), current flow analysis using temperature profiles, nano-technology, microelectromechanical systems (MEMS), temperature profile analyses of large areas using inexpensive pyrometers, heat source propagation analysis, and heat flux and convection analysis.

System 10 includes a device under test 12, which in this example is a semiconductor device. A temperature sensor 14 is positioned relative to device 12 such that it may measure a temperature of the surface of semiconductor device 12 at a plurality of locations while device 12 is operating. Although a variety of temperature sensors may be used, a pyrometer is one particularly suitable temperature sensor. Pyrometers are well known in the art and generally measure the temperature of a surface through use of a beam of infrared light. Device 12 is positioned, in this example, on a probe chuck 16. Probe chuck 16 positions device 12 in an X-Y coordinate system with respect to pyrometer 14 such that temperature sensor 14 may sample the temperature of device 12 at any desired location of device 12. Based on a sampled temperature, temperature sensor 14 provides a temperature output signal 18 to a computer system 22. In conjunction, probe chuck 16 provides an X-Y coordinate output signal 20 indicative of the position on device 12 at which the temperature was sampled to computer system 22. Such a signal may originate from an X-Y coordinate sensor located on probe chuck 16, or through other suitable techniques. According to one embodiment, probe chuck 16 moves at a rate that, in conjunction with the sampling rate of temperature sensor 16, provides a temperature profile having a resolution of less than one micron.

Computer system 22 operates generally to receive a temperature output signal 18 and corresponding location signal 20 and, for each location at which temperature sensor 14 sampled a temperature of device 12, to construct a temperature profile of device 12. As described in greater detail below, computer system 22 compares this constructed temperature profile of device 12 to a reference profile of device 12. The reference temperature profile of device 12 refers to a temperature profile of a device 12 when the device is operating properly. In this example, computer system 22 includes an input/output interface card 24 for receiving temperature output signal 18 and coordinate output signal 20. The received information is then provided to other portions of computer system 22, which may generate a temperature difference between the constructed temperature profile and the reference temperature profile for graphical display on a display 26. Such a graphical image is depicted in FIG. 1A as graph 28.

As described above, the device to be tested 12 is a semiconductor device in this example. However, device 12 may be any suitable device for which a temperature profile may be indicative of the operation of the device. The teachings of the invention recognize that semiconductor devices are particularly sensitive to temperatures, and conversely, the resulting temperature of the semiconductor device is particularly sensitive to the proper operation of the semiconductor device. Thus, by comparing a temperature profile of a properly operating semiconductor device to a temperature profile of an improperly operating semiconductor device, a determination can be made of a location of potential defects in the improperly operating semiconductor device.

As described above, temperature sensor 14 may be a pyrometer, or other suitable temperature device. A pyrometer is well known in the art and generally uses a beam of infrared light to sample a temperature. One aspect of a pyrometer that makes it particularly suitable for the present application is that it can sample a temperature at a high rate of speed, allowing very fine resolution of temperature with respect to location. In one example, pyrometer 14 samples a temperature of the surface of the semiconductor device 12 at a rate of over 100 times per second. It should be noted, however, that much slower sampling rates may be utilized if a lower resolution for the constructed temperature profile is acceptable, or if the speed at which the semiconductor device is scanned is sufficiently slow. It should also be noted that the area of semiconductor device 12 over which pyrometer 14 determines a temperature for a given temperature sample may be greater than the desired resolution of the constructed temperature profile. The constructed temperature profile will have a spatial resolution defined by the sampling rate of temperature sensor of pyrometer 14 and the speed at which the semiconductor device is scanned relative to the temperature sensor.

Probe chuck 16 is a positioning system that allows highly accurate positioning of a device, and in this case, semiconductor device 12. Such positioning systems are well known in the art, one example of which is the CM500 probe station from Signatone; however, any suitable positioning system that can position a device at an accurately known location may be utilized. It should also be noted that although FIG. 1A illustrates positioning of semiconductor device 12 by probe chuck 16 such that it moves relative to temperature sensor 14, probe chuck 16 may be conversely used to successively move temperature sensor 14, with semiconductor device 12 remaining stationary. According to one embodiment, probe chuck 16 moves essentially continuously while temperature sensor 14 samples a temperature at the instantaneous location underlying the temperature sensor 14. However, in one embodiment probe chuck 16 may involve repeated starting and stopping, such that the temperature may be measured while the probe chuck is stationary. The teachings of the invention recognize that utilizing a sufficient sampling rate for temperature sensor 14 with a sufficiently slow continuous, or start-stop, relative movement between temperature sensor 14 and semiconductor device 12 allows for almost infinite resolution of a constructed temperature profile for semiconductor device 10. Such a high resolution profile allows pinpoint identification of a location in device 12 having a potential defect, by comparison to a similar profile for a properly operating semiconductor device.

Temperature output signal 18 and X-Y coordinate output 20 are illustrated as two separate signals originating from two different locations; however, it will be recognized that these signals may originate from a common location and may be provided in any suitable manner to computer system 22.

Computer system 22 in one example is a personal computer; however, any suitable computer may be utilized that may accept signals indicative of location and temperature and generate a temperature profile based on the received indications. Additional details of computer system 22 are described in greater detail below in conjunction with FIG. 1B.

In operation, a temperature profile for a semiconductor device under test is generated, in this example, by mounting the semiconductor device 12 on a probe chuck 16. A pyrometer 14 is positioned in a location with respect to semiconductor device 12 such that it may measure a temperature of a surface of semiconductor device 12. Then, probe chuck 16 successively moves semiconductor device 12 at a rate of speed that allows pyrometer 14 to sample the temperature at a desired corresponding location of semiconductor device 12. A temperature signal 18 corresponding to the sampled temperature and a corresponding location signal 20 corresponding to the location at which the temperature on semiconductor device 12 was sampled are provided to computer system 22 using, in this example, an I/O card 24. These signals are accumulated and a temperature profile for semiconductor device 12 is generated. This temperature profile may then be compared to a reference temperature profile illustrating a temperature profile for a semiconductor device when it is operating properly. Differences between the two temperature profiles may be examined, including the use of statistical techniques, to generate a graphical depiction of statistically significant temperature differences between the two. This graphical depiction may then be displayed, as indicated by reference numeral 28. In one particular example, the temperature difference profile may be laid over a graphical depiction of semiconductor device 12, such that viewing of the resulting image allows visual location of a potential defect.

Thus, according to the teachings of the invention, a potential location of a defect in a semiconductor device may be identified through comparison of a generated temperature profile to a reference temperature profile. The generated temperature profile may be generated through the use of scanning a temperature sensor with respect to the device at a rate that provides a desired resolution for the resulting temperature profile. Certain advantages flowing from the teachings of the invention include the ability to quickly locate a potential location of a defect in a semiconductor device, which may otherwise be a time-consuming process. Additional details of sample embodiments of the invention are described below with respect to FIGS. 1B through 2B.

Figure 1B:
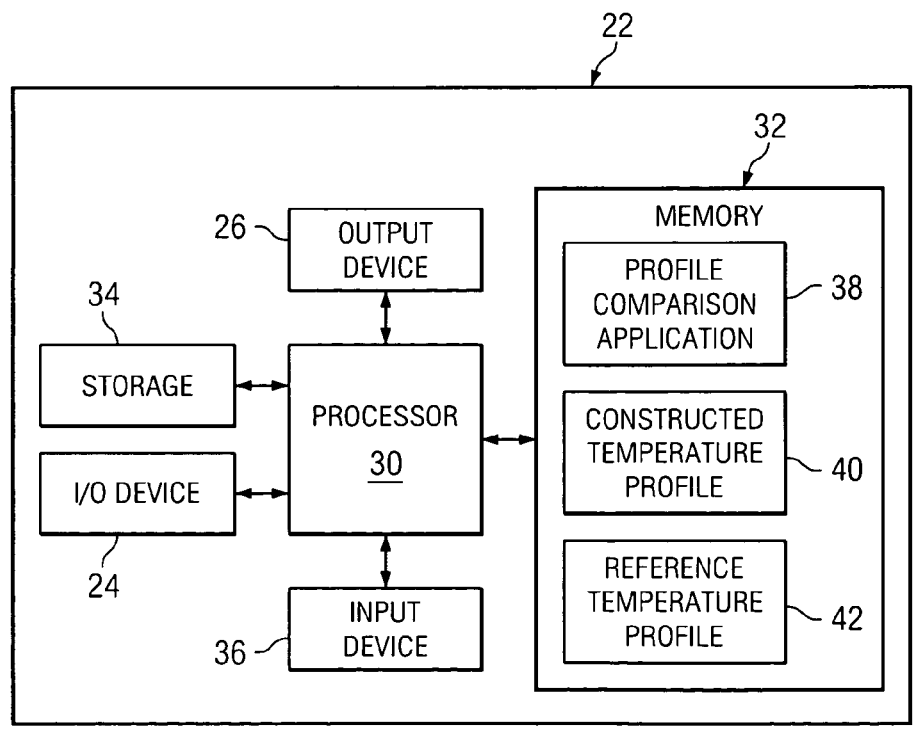
FIG. 1B is a block diagram illustrating additional details of an example of the computer system of FIG. 1A.

FIG. 1B is a block diagram illustrating example details of computer system 22, illustrated in FIG. 1A. In this example, computer system 22 includes a processor 30 coupled to associated memory 32 and storage 34. Computer system 22 also includes output device 26, such as display 26 of FIG. 1A, and an input device 36, as well input/output device 24. Although a particular implementation of computer 22 is described here, it will be recognized that any suitable computer system that may receive indications of temperature and location and use associated algorithms may be utilized without departing from the teachings of the invention.

Processor 30 may be any suitable processor, examples of which include conventional processors from Intel and AMD as well as yet to be developed processors. Storage 34 may comprise hard disks or other suitable media for long-term storage of data. Memory 32 may store various applications as well as data and may comprise random access memory or other suitable forms of memory. In this example, memory 32 stores a temperature conversion application 38 as well as the constructed temperature profile 40 and the reference temperature profile 42; however, these applications and profiles may also be stored in storage 34 or in other locations, including locations apart from computer system 22.

Output device 26 may be any suitable output device such as a display, printer, or other output apparatus that allows data to be conveyed to a user. Input device 36 may comprise a keyboard, a mouse, or other output device that allows a user to input information into computer system 22.

Temperature conversion application 38 generates a comparison of constructed temperature profile 40 and reference temperature profile 42. This comparison may involve subtracting one from the other as well as a statistical analysis of the difference to determine what temperatures correspond to statistically different temperatures. Reference temperature profile 42 may include, in addition to a particular temperature profile for a properly operating reference device, statistical data such as standard deviations used to assess whether differences between the reference temperature profile and the constructed temperature profile are significant. Example acts associated with operation of temperature conversion application 38 are described in greater detail below in conjunction with FIG. 2B.

FIG. 2A is a flowchart illustrating a method 100 for determining a location of a potential defect in a semiconductor device according to the teachings of the invention. Method 100 may be implemented by the system of FIG. 1A or by using other suitable apparatuses and systems. The method begins at step 102. At step 104 the surface of a device under test is scanned by a temperature sensing device. In one example, the temperature sensing device is a pyrometer; however, other suitable temperature sensors may be used. In one particular example, the device under test is a semiconductor device; however, the device under test may be any suitable device for which it may be desired to locate a potential defect based upon the temperature profile of the device.

While scanning, a temperature of the device under test is measured at a plurality of locations, as indicated by reference numeral 106. The measured temperature and the corresponding coordinates of the location of the temperature measurement on the device under test are associated at step 108 and may be provided to computer system for analysis. Alternatively, this information may be output for direct analysis by a user. Step 108 also includes constructing a temperature profile for the device under test.

At step 110 the constructed temperature profile is compared to a reference temperature profile. This comparison provides information relevant to how a properly operating device differs in temperature profile from an improperly operating device. Example acts associated with this comparison are described in greater detail below in conjunction with FIG. 2B. At step 112, statistically significant temperature differences between the reference temperature profile and the constructed temperature profile may be graphically displayed. In one particular example, the difference in temperature profile is displayed graphically overlying a depiction of the device under test, allowing visual identification of locations at which the temperature locations on the device at which the associated temperature profile significantly differs from the reference profile. This allows an efficient identification of the location of a potential defect in the device under test. The method concludes at step 114.

FIG. 2B illustrates example acts associated with step 110 of FIG. 2A of comparing the constructed temperature profile to a reference temperature profile. The method begins at step 120. At step 122 the reference temperature profile is subtracted from the constructed temperature profile. Alternatively the constructed temperature profile may be subtracted from the reference temperature profile. Further, other comparison techniques may be utilized rather than simple subtraction of one profile from the other. At step 124 a statistical analysis is performed on the difference profile generated at step 122. This may involve use of the statistical data concerning the reference temperature profile such as standard deviations associated with the various temperatures. At step 126 a profile of statistically significant temperature differences is generated for the semiconductor device. This facilitates an efficient identification of potential locations of a defect in a device. The method concludes at step 128.

Thus, according to the teachings of the invention a system and method are provided that allow efficient identification of a location in a device, such as a semiconductor device, that may correspond to potential defects based upon the temperature profile of the device.

Although the present invention has been described with several embodiments, a myriad of changes, variations, alterations, transformations, and modifications may be suggested to one skilled in the art, and it is intended that the present invention encompass such changes, variations, alterations, transformation, and modifications as they fall within the scope of the appended claims.

What is claimed is:

1. A method for determining the location of a potential defect in a semiconductor device comprising:
   scanning a surface of the semiconductor device with a temperature sensor while operating the semiconductor device;
   measuring a temperature of a semiconductor device by the temperature sensor at a plurality of locations while scanning;
   constructing a temperature profile for the semiconductor device based on the measured temperatures; and
   comparing the constructed temperature profile to a reference temperature profile to determine a location of a potential defect in the semiconductor device.

2. The method of claim 1, wherein scanning a surface of the semiconductor device with a temperature sensor comprises moving the temperature sensor with the respect to the semiconductor device.

3. The method of claim 1, wherein scanning a surface of a semiconductor device with a temperature sensor comprises moving the semiconductor device with respect to the temperature sensor.

4. The method of claim 3, wherein moving the semiconductor device with respect to the temperature sensor comprises moving the semiconductor device by an X-Y chuck.

5. The method of claim 1, wherein scanning a surface of the semiconductor device comprises scanning a surface of the semiconductor device with a pyrometer.

6. The method of claim 1, wherein measuring a temperature of a semiconductor device by the temperature sensor comprises sampling a temperature of the semiconductor device at a rate of at least 100 times per second.

7. The method of claim 1, wherein measuring a temperature of a semiconductor device by the temperature sensor at a plurality of locations while scanning comprises measuring at a plurality of intervals in location of less than one micron.

8. The method of claim 1, wherein comparing the constructed temperature profile to a reference temperature profile comprises subtracting one of the constructed temperature profile and the referenced profile from the other one of the constructed temperature profile and the reference profile.

9. The method of claim 1, wherein comparing the constructed temperature profile to a reference temperature profile comprises comparing the constructed temperature profile to a reference profile indicative of a properly operating semiconductor device.

10. The method of claim 1, wherein comparing the constructed temperature profile to a reference temperature profile comprises determining any statistically significant differences between the temperature profiles and further comprising graphically displaying the location on the semiconductor device of any of the statistically significant differences.

11. The method of claim 1, wherein scanning comprises continuously moving either or both of the temperature sensor and the semiconductor device with respect to the other.

12. A method of examining an article comprising:
scanning a surface of the article with a temperature sensor;
measuring the temperature of the article at a plurality of locations while scanning, the plurality of locations being at intervals of less than one micron;
constructing a temperature profile for the article based on the measured temperatures; and
comparing the constructed temperature profile to a reference temperature profile associated with the article and determining any statistically significant differences between the temperature profiles and further graphically displaying the location on the article of any of the statistically significant differences.

13. The method of claim 12, wherein scanning a surface of the article with a temperature sensor comprises moving the article with respect to the temperature sensor.

14. The method of claim 12, wherein scanning a surface of the article comprises scanning a surface of the article with a pyrometer.

15. The method of claim 12, wherein measuring a temperature of the article by the temperature sensor comprises sampling the temperature of the article at a rate of at least 100 times per second.

16. A system for analysis of a semiconductor device comprising:
a temperature sensor operable to sample a temperature of the semiconductor device at a rate of at least 100 times per second;
a positioning system operable to support one of the temperature sensor and the semiconductor device, operable to operate the semiconductor device, and further operable to scan the temperature sensor over the semiconductor device while the semiconductor device under test is operating; and
a computer system operable to:
receive respective samples of a temperature at a plurality of locations of the article measured by the temperature sensor and an indication of the respective locations;
generate a temperature profile for the article based on the received samples of temperature and indications of location; and
compare the generated temperature profile to a reference profile associated with the article.

17. The system of claim 16, wherein the temperature sensor is a pyrometer.

18. The system of claim 16, wherein the article is a semiconductor device.

19. The system of claim 16, wherein the computer is further operable to generate data defining a graphical image of the location on the article of any statically significant differences between the generated temperature profile and the reference temperature profile.

* * * * *